United States Patent
Schepis et al.

(10) Patent No.: US 8,958,886 B2
(45) Date of Patent: Feb. 17, 2015

(54) METHOD AND APPARATUS TO INCREASE TACTILE SENSTIVITY AND PROPRIOCEPTION IN HUMANS

(71) Applicant: Kimberly-Clark Worldwide, Inc., Neenah, WI (US)

(72) Inventors: Eric Anthony Schepis, Alpharetta, GA (US); Matthew John Valaskey, Neenah, WI (US); Shawn Jeffery Sullivan, Neenah, WI (US); Martha Lillian Tate, Sandy Springs, GA (US); Kaiyuan Yang, Cumming, GA (US); Martin S Shamis, Alpharetta, GA (US); WonYeong Sohn, Seoul (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/107,187

(22) Filed: Dec. 16, 2013

(65) Prior Publication Data

US 2014/0188194 A1     Jul. 3, 2014

Related U.S. Application Data

(60) Provisional application No. 61/747,523, filed on Dec. 31, 2012.

(51) Int. Cl.
*A61N 1/00* (2006.01)
*A61N 1/36* (2006.01)
*A61N 1/04* (2006.01)

(52) U.S. Cl.
CPC .......... *A61N 1/36103* (2013.01); *A61N 1/0456* (2013.01)
USPC .......................................................... 607/62

(58) Field of Classification Search
USPC .......................................................... 607/62
See application file for complete search history.

(56) References Cited

U.S. PATENT DOCUMENTS

| | | | |
|---|---|---|---|
| 2008/0097530 A1* | 4/2008 | Muccio et al. | 607/3 |
| 2009/0290743 A1* | 11/2009 | Carroll | 381/385 |
| 2010/0030299 A1* | 2/2010 | Covalin | 607/46 |
| 2010/0326843 A1* | 12/2010 | Zhang et al. | 205/777.5 |
| 2013/0072835 A1* | 3/2013 | Harry et al. | 601/46 |

* cited by examiner

*Primary Examiner* — Robert N Wieland
(74) *Attorney, Agent, or Firm* — Denise L. Stoker

(57) ABSTRACT

An article for transcutaneously applying electrical stimulation to sensory receptors. The article is a support to which an electrode pair, a positive and corresponding negative electrode, is attached. Leads are electrically attached to each of the positive and negative electrodes, wherein each lead has an insulated coating. A controller is electrically attached to the leads for delivering monophasic or biphasic electrical stimulation at a single frequency. A power supply is electrically connected to the controller, and may be attached to the support. The article may be a sock, a glove, a harness or an insole.

20 Claims, 11 Drawing Sheets

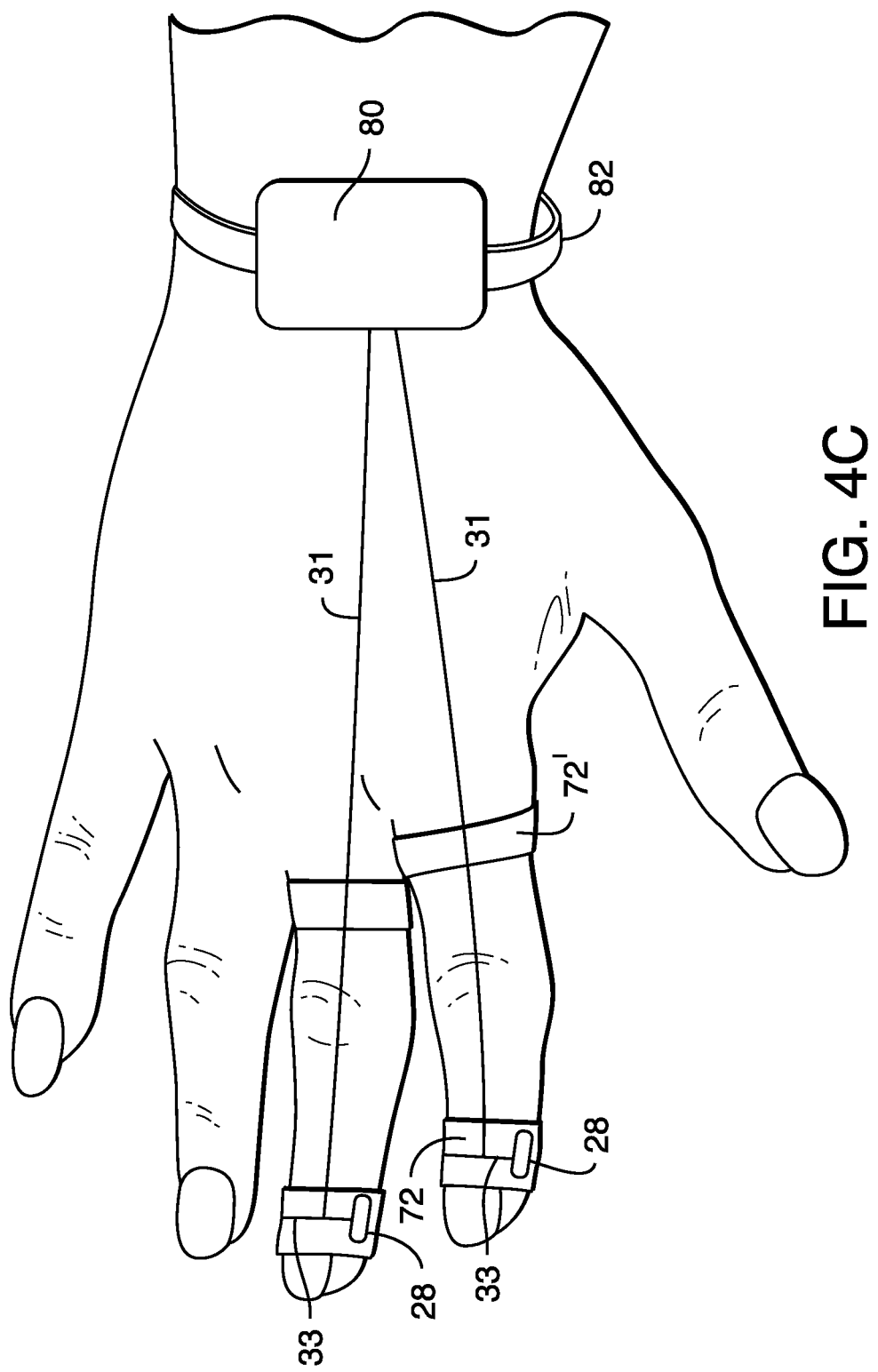

METHOD AND APPARATUS TO INCREASE TACTILE SENSTIVITY AND PROPRIOCEPTION IN HUMANS

CROSS REFERENCE TO RELATED APPLICATION

This application claims the benefit of U.S. Provisional Application No. 61/747,523, filed on Dec. 31, 2012. The entirety of Application No. 61/747,523 is incorporated herein by reference.

BACKGROUND OF THE DISCLOSURE

The senses of touch and proprioception describe the faculty by which external forces are perceived by the body, and how the body recognizes its position in space, respectively. The loss or diminishment of these senses challenges how people interact with each other and their environment.

The complications associated with tactile and proprioceptive insensitivity are wide-ranging; mild levels of insensitivity may go unnoticed, while more severe levels can lead to hand and joint dysfunction, falls, pain, and sometimes even death. People who are readily affected by tactile insensitivity include those with neuropathy, stroke, the elderly, and those with diabetes or who frequently use vibrating hand tools, or work in cooler environments. Others experience a temporary loss of tactile acuity too, including those who wear personal protective equipment (i.e. surgeons).

Stochastic resonance technologies have been used to enhance or restore tactile and proprioceptive sensitivity in humans. Stochastic resonance is a phenomenon whereby the application of electrical or mechanical noise to a non-linear system, such as the human body, can heighten the body's sensory capabilities. Though the mechanisms responsible for stochastic resonance in humans remain unclear, studies show that the application of noise to the skin can increase tactile sensitivity in the nearby regions of the body, enabling one to sense mechanical stimuli of relatively low intensity. Similarly, in studies of elderly subjects, noise delivered transcutaneously to the tendons and metatarsal joints in the foot decreased postural sway and caused a heightened sense of proprioception.

Noise used to elicit the stochastic resonance phenomenon in humans has been either electrical or mechanical in nature, and delivered with multiple frequencies between 0 and 1000 Hz (white or Gaussian noise) at imperceptible levels of intensity. Stochastic resonance technologies face practical limitations. The noise delivery systems and stimulators that are used today are too complicated and cumbersome to be incorporated into an apparatus and used beyond the confines of the laboratory. For instance, a mechanical stochastic resonance system delivers noise via piezoelectric or vibratory shaker apparatuses that require large circuitry. The mechanical apparatus needs to be placed over-top of the skin region that is intended to be sensitized. This necessarily limits the skin area that can be affected. An electrical stochastic resonance apparatus however, delivers noise through surface electrodes that are small, flexible and that can be positioned farther away from targeted receptors. Despite this however, the complicated stimulating paradigm causes the stimulation device and controller to be too large for practical purposes.

Thus, there presently exists a need for an apparatus that can increase tactile and/or proprioceptive sensitivities that is practical for use in the field or at home.

SUMMARY OF THE DISCLOSURE

In accordance with one embodiment of the present disclosure, there is an article for transcutaneously applying electrical stimulation to sensory receptors. The article is a support to which an electrode pair, a positive and corresponding negative electrode, is attached. Single leads are electrically attached to each of the positive and negative electrodes, wherein each single lead has an insulated coating. A controller is electrically attached to each single lead for delivering monophasic or biphasic electrical stimulation at a single frequency between 150 Hz to 350 Hz, and at a current between 0.1 mA to 5 mA. A power supply is electrically connected to the controller, and may be attached to the support.

In one aspect, the article is a sock, a glove or an insole. The sock, the glove or the insole may be constructed from a molded material, a nonwoven material, a woven material or a combination thereof.

In another aspect the article of the present disclosure is a harness.

In a further aspect, the article, in the sock or glove form, may include one or more dome members, each having a concave surface to which the positive electrode or the negative electrode is attached. Optionally, an electrolytic gel or paste is applied to the concave portion so that it covers the corresponding positive or negative electrode.

In another embodiment of the present disclosure, a method of transcutaneously stimulating sensory receptors of the human body includes the following steps: contacting the intact skin of a human with an electrode pair comprising a positive electrode spaced apart from a negative electrode; and delivering monophasic or biphasic electrical current to the positive electrode at a single frequency of between 150 Hz to 350 Hz. The electrical current may be less than 5 mA. The electrical current may be delivered in square pulses having a duration of about 100 µs.

Other features and aspects of the present disclosure are set forth in greater detail below.

BRIEF DESCRIPTION OF THE DRAWINGS

FIG. 4C is a plan view of a harness system according to one embodiment of the present disclosure, showing the two harnesses of FIG. 4A attached to a hand and a controller.

DETAILED DESCRIPTION

Figure 1:
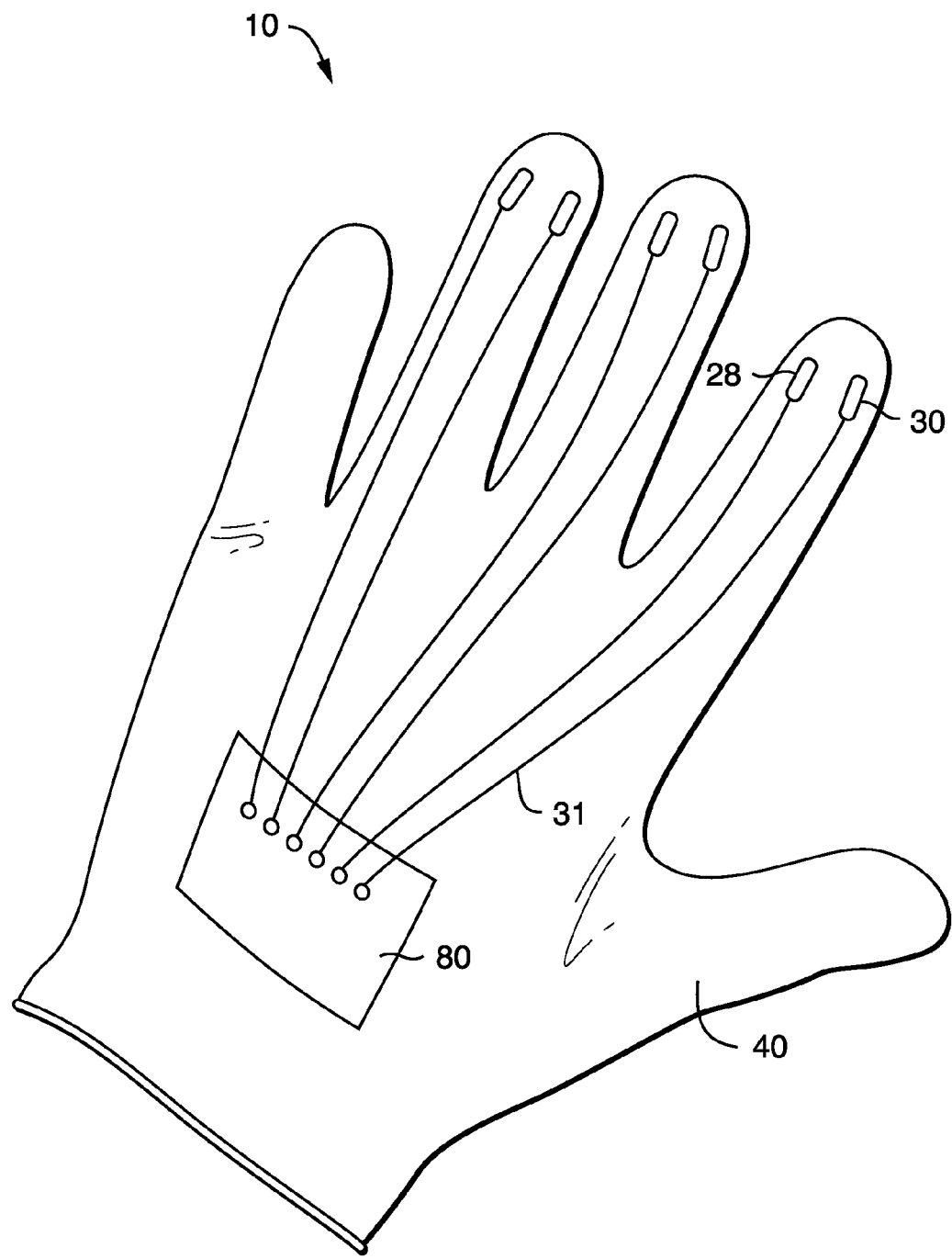
FIG. 1 is top perspective view of one embodiment of a glove according to the present disclosure.
Figure 2:
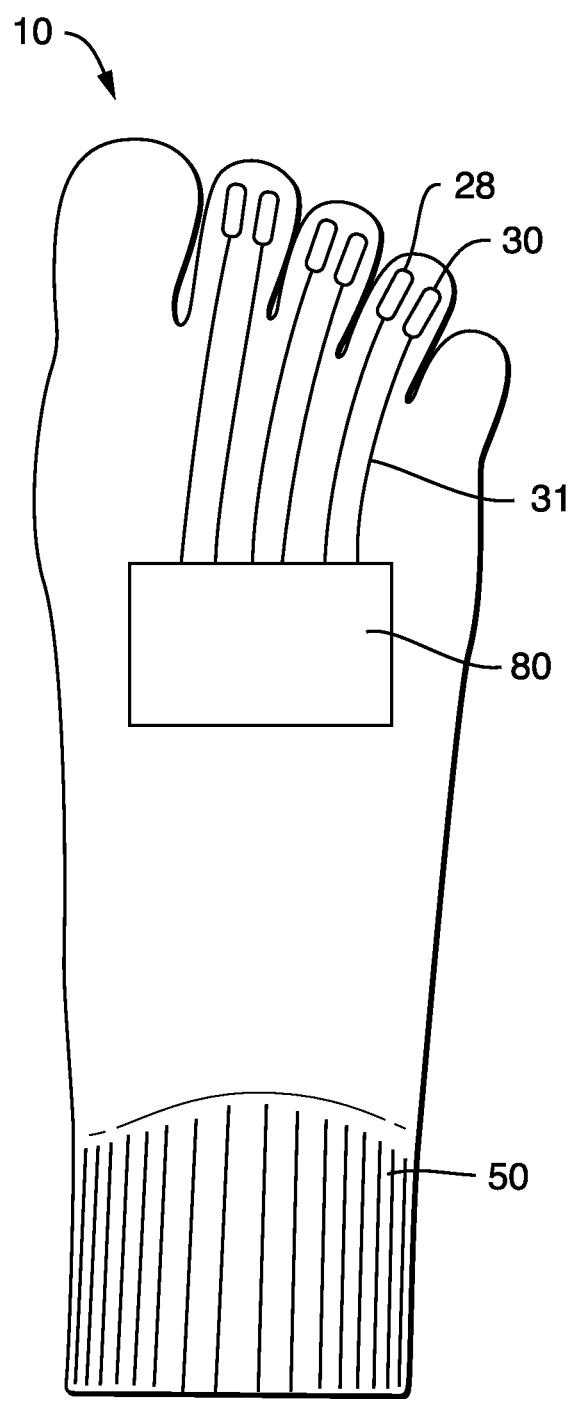
FIG. 2 is a plan view of one embodiment of a sock according to the present disclosure.

Reference now will be made in detail to various embodiments of the disclosure, one or more examples of which are set forth below. Each example is provided by way of explanation, not limitation of the disclosure. In fact, it will be apparent to those skilled in the art that various modifications and variations may be made in the present disclosure without departing from the scope or spirit of the disclosure. For instance, features illustrated or described as part of one embodiment, may be used on another embodiment to yield a still further embodiment. Thus, it is intended that the present disclosure cover such modifications and variations.

"Molded" as used herein refers to a type of structure that may be formed around a mold, such as a glove mold dipped in a liquid that is solidified. The solidified material is removed from the mold, retaining the shape of the glove mold.

Nonwoven material is defined as a class of fabrics produced by attaching fibers (e.g. such as by chemical or mechanical means), or both. The nonwoven fabric is made by mechanical, chemical, thermal, or solvent means, or with an adhesive, or any combination of these, and is distinct from woven, knitted or tufted materials. Nonwoven fabrics may be made from synthetic thermoplastic polymers or natural polymers such as cellulose. For example, cellulosic tissue is one type of a nonwoven material.

The method and apparatus of the present invention may be used to increase tactile and proprioceptive sensitivities. The apparatus may be in the form of a sock, a glove, an insole or a harness system having electrode pairs that electrically stimulate sensory receptors in the toes, fingers or the sole a foot, as appropriate. Generally, the electrical stimulation is not perceptible, and may be delivered in monophasic or biphasic square waves at a single frequency, desirably 250 Hz. The electrodes may be made from a metal or carbon paste and polymeric binder composition printed onto a support (e.g. a glove). By employing the method and apparatus of the present disclosure, the problems presented by using multiple frequencies (noise) are prevented.

It is important to distinguish the difference between the electrical stimulation of sensory receptors versus nerves. Herein, the electrical stimulation is acting on the sensory receptors that are located in the skin to enable tactile sensitization, and on the receptors in the tendons and joints to enhance proprioception. Sensory receptors play an important role of transducing energy (i.e. mechanical, chemical, thermal, etc.) into neural signals that are transmitted through the nerves to the spinal cord. Importantly, sensory receptors are self-contained structures that are differentiated in anatomy and physiology from their attached nerve fiber. Herein, we are using the stimulation to facilitate the activation of sensory receptors, enabling them to generate action potentials with less energy.

Apparatus

The apparatus is constructed from an electrode pair connected to leads, which in turn are connected to a controller and a power supply. Each of these components is described in detail below.

Electrode Pair

At least two electrodes (i.e. electrode pair) are needed to deliver electrical stimulation. The cathode or stimulating electrode, delivers a positive-going pulse that attracts negatively-charged ions within the tissue. The anode or ground electrode delivers a negative-going pulse that attracts positively-charged ions. The movement of ions within the tissue approximates a current flow, and likely acts on sensory receptors by modulating their receptor potential and sensitizing the organ. The electrodes (described herein) are attached to insulated leads that pass to the stimulator.

The electrodes can be made from a variety of conductive materials. Such materials include carbon, metals (e.g., platinum, palladium, gold, tungsten, titanium, etc.), metal-based compounds (e.g., oxides, chlorides, etc.), metal alloys, conductive polymers, combinations thereof, and the like. Particular examples of carbon electrodes include glassy carbon, graphite, mesoporous carbon, nanocarbon tubes, fullerenes, etc.

The electrodes may be in the form of a film. Thin films of the conductive materials may be formed by a variety of methods including, sputtering, reactive sputtering, physical vapor deposition, plasma deposition, chemical vapor deposition (CVD), printing, spraying, and other coating methods. For instance, carbon- or metal-paste based conductive materials are typically formed using screen printing. Metal based electrodes are typically made using standard sputtering or CVD techniques. In other aspects, the electrodes may be formed by stamping or cutting thin sheets of desired metals as is known in the art.

Each electrode may be unique in shape and size, or the electrodes may be identical in those respects. Any variety of shapes may be used (e.g. rectangle, circle, oval, random, etc.) The size of an electrode is determined by the available skin area. In general, larger electrodes will enable larger areas of sensitization.

In one desirable aspect of the disclosure, electrodes are screen printed onto the support. The electrodes may be made with a carbon paste and polymeric binder, mixed together with a volatile solvent to create a screen printable "ink".

The resulting thickness of the screen printed electrodes (once the volatile has evaporated) is between 0.5 and 100 microns, or between 0.5 and 50 microns, or between 0.5 and 20 microns, or between 0.5 and 10 microns, or between 0.5 and 1 micron. These thicknesses are desirable for the other aforementioned types of electrodes that may be employed.

In the alternative, the electrodes may be constructed from woven or nonwoven threads made from conductive fibers. The threads may have a round or rectangular cross-section and may have the same thickness as described above for the screen printed electrodes. The threads may be woven into the material from which a support is made.

In yet another alternative, the electrodes may have a laminate structure. Again, such electrodes have the same thickness as the screen printed electrodes.

Leads

The leads conduct electricity from the controller to the electrodes, and can be made from a material that is the same or different than the material of the electrode pair.

In one desirable aspect, leads are screen printed onto a support. Such leads are made with a silver or silver chloride paste, and a polymeric binder. Volatile solvents are added to this composition to create an "ink" that can be screen printed either over the top of the previously printed carbon leads, or in place of the carbon leads. The resulting thickness of the screen printed leads (once the volatile has evaporated) is between 0.5 and 100 microns, or between 0.5 and 50 microns, or between 0.5 and 20 microns, or between 0.5 and 10 microns, or between 0.5 and 1 micron.

The leads are electrically insulated so that they do not short in the presence of moisture. If the leads are screen printed leads, an insulation coating is placed over the top of the lead, creating a seal between the support immediately surrounding the lead and the coating. If the leads are threads or laminate strips, the entire thread/strip may be coated with insulation material prior to placement onto the support of before integration therewith.

In one aspect, the leads are coated with a photoresist material such as organic compounds that can be altered by exposure to light of a particular wavelength or range of wavelengths. This material is necessarily flexible as the leads need to remain flexible. An exemplary coating technique includes depositing a layer of a photoresist over the leads. Exposure to light makes the photoresist material less susceptible to removal by chemical agents. After the layer of photoresist material is applied, it is exposed to light, or other electromagnetic radiation, through a mask.

Support

Referring now to FIGS. 1-4, a support 10 such as a glove 40, sock 50, insole 60 or harness 70 are exemplary articles to which the electrodes 28, 30 may be attached (e.g. adhesively or mechanically) or even integrated (e.g. a woven glove made with conductive and non-conductive threads). These articles may be molded from a polymeric material, a woven material, a nonwoven material and combinations thereof.

Molded gloves or socks may be made by conventional methods known in the art, such as by dipping, spraying or otherwise coating a mold with a desired material and turning the article inside out after placement of the electrodes 28, 30 and curing the material (not necessarily in that order). For example, gloves 40 or socks 50 may be made in a manner as described in U.S. Pat. No. 4,521,365 issued to Kurtz et al. or by U.S. Pat. No. 5,693,401 issued to Sommers, both of which are incorporated herein by reference to the extent they are consistent with the present disclosure.

Figure 5:
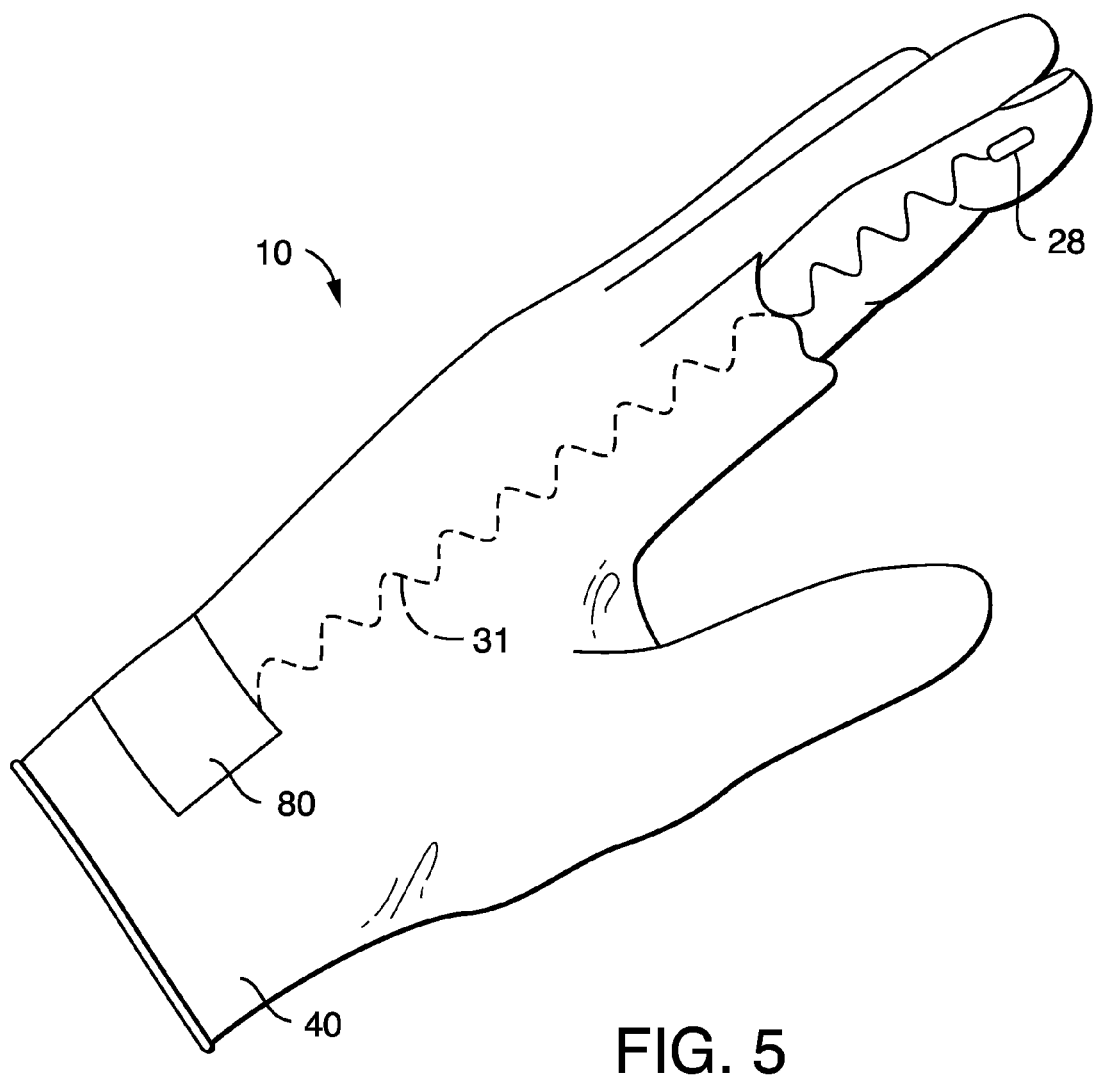
FIG. 5 is a side perspective view of another embodiment of a glove according to the present disclosure, with a cutaway portion showing the body-facing surface and electrode.

In one aspect, a support is in the shape of a sock 50 or glove 40 that is molded from nitrile, acrylic or latex. Because these materials are flexible and elastic, the leads attached to these materials are necessarily flexible as well. Elasticity is not inherent to the materials to which the leads 31 are made. To create pseudo-elasticity in what might be a non-elastic material, the lead 31 may be applied to the support surface in a sawtooth or sinusoidal pattern as seen in FIG. 5, showing a support 10 in the form of a nitrile glove having an electrode 28 and lead 31.

One advantage of an elastomeric sock or glove is that it can be fit to a person's foot or hand in a way that creates constant pressure. This makes the electrode contact constant, which is greatly desired. In one aspect, the sock or glove is sufficiently elastic so that when attached to the user's body, it is capable of applying forces upon the body tissue and compliantly responding to force resultant from body motion.

Figure 6A:
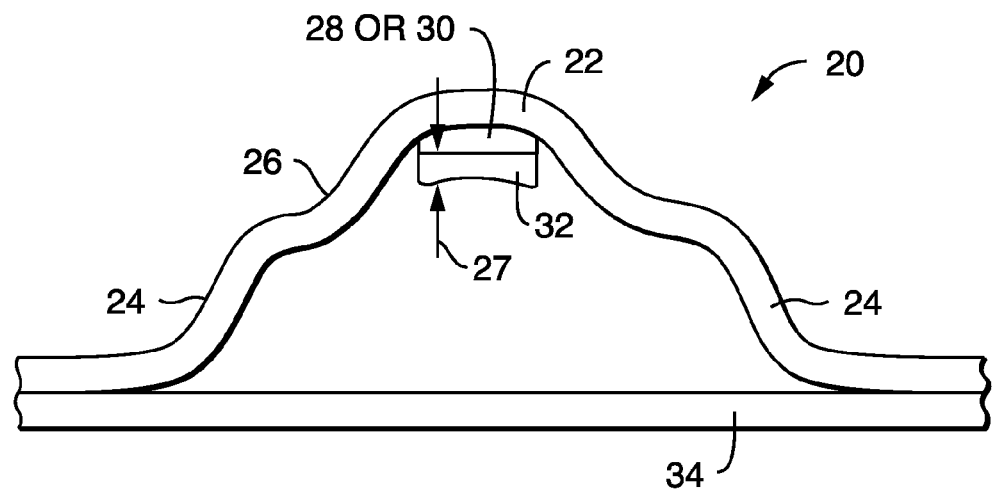
FIGS. 6A and 6B are side cross-sectional views of a dome member according to the present disclosure in an initial state and a depressed state, respectively.
Figure 6B:
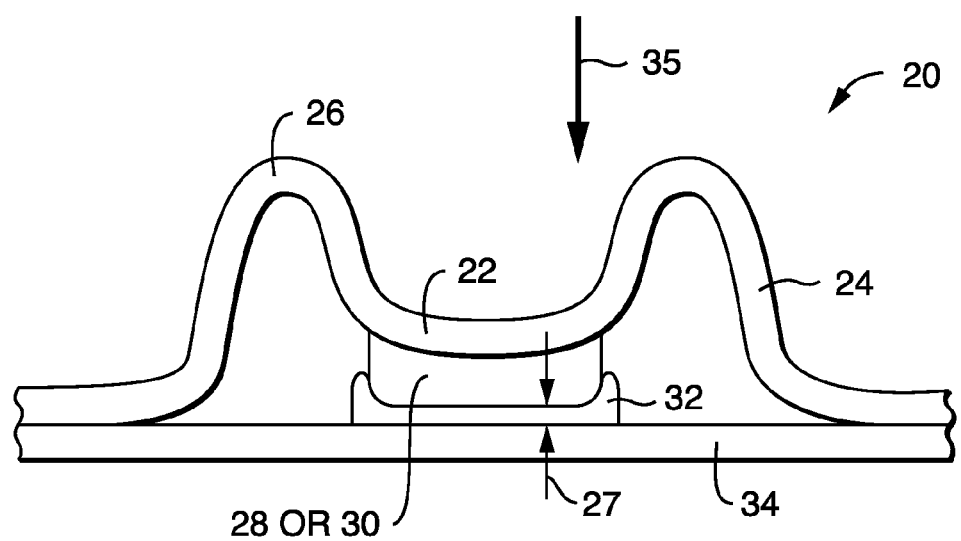

Referring to FIGS. 6A and 6B, a snugly fitting elastomeric article may be more difficult to don without disrupting the placement of the electrode pair 12 on the body-facing surface 16 of the article, support 10. In one aspect, the difficulty that may be experienced when donning an article having electrodes located therein can be alleviated with dome members housing electrodes 28. The dome members 20 are attached to the bodyfacing surface of the glove or sock in desired locations such as at the tips or the fingers or toes.

A single dome member 20 is shown in an initial state and a depressed state, respectively. A plan view (not shown) of the dome member 20 resembles circular-shaped blister. Desirably, the dome member 20 features a top portion 22, and side 24 connected to top portion 22 by an optional concave portion 26. The purpose of concave portion 26 is to create a stress concentration in the dome member 20. When force is applied to the top portion in direction 35 (toward the user's skin 34), the presence of the stress concentration ensures that the dome member stays in a depressed position as seen in FIG. 6B. Further, it ensures that the top portion will depress uniformly, and that the side 24 will remain in an upright supportive position. Dome member 20 may be made from a plastic material, capable of deforming into a new shape without spontaneously returning to the pre-deformed shape.

Under the top portion 22 of dome member 20 is a single electrode, which may be a positive electrode 28 or a negative electrode 30. Electrode 28/30 is adhesively attached to the top portion 22, or embedded therein. The lead corresponding to the electrode may connect at the top portion of the dome through a small aperture, not shown. When the dome member 20 is depressed, the electrode 28/30 is at skin level so it makes contact with the skin 34.

In one aspect, a coupling media such as an electrically conductive gel or paste may be applied to the electrode to enhance the conductivity of the skin and/or lower impedance. Desirably, the electrolytic gel or paste 32 coats the bodyfacing surface of electrode 28/30 so that when dome member 20 depressed, the gel or paste 32 enhances the contact between the skin 34 and the electrode 28/30. This coating of gel or paste 32 may be about 0.5 mm to about 1.5 mm thick prior to depressing the dome 20. FIG. 6B shows the gel or paste 32 between the electrode 28/30 and skin 34. The thickness 27 may vary from 0 mm to the approximate thickness it was prior to the depression of dome 20. Examples of conductive pastes include TEN20 conductive paste from Weaver and Company, Aurora, Colo., and ELEFIX Conductive Paste from Nihon Kohden with offices at Foothill Ranch, Calif. Examples of conductive gels include SPECTRA 360 Electrode Gel from Parker Laboratories, Inc., Fairfield, N.J., or ELECTRO-GEL from Electro-Cap International, Inc., Eaton, Ohio.

Alternatively and/or additionally, prior to making skin contact with electrodes 28/30, one or more skin moisturizers, humectants or the like may be applied to the skin for the purpose of enhancing the conductivity of the skin and/or lowering impedance of the skin.

In another aspect, the sock, glove or insole may be made from a woven material. A woven structure provides the opportunity to weave insulated leads into very fabric from which these articles are constructed. Because the leads 31 are not elastomeric, the selected weave is such that when an appendage in sock or glove moves, or when the insole is flexed, the resulting tensile or compressive forces do not cause the lead to fail mechanically. Thus, a knitted fabric may be more desirable than a flat-weave fabric as many knitted weave patterns can stretch even when the threads used to make the fabric are not elastomeric. However, a flat-weave fabric (or knitted fabric) of conductive materials may have leads stitched or glued thereon in a pattern that can accommodate tensile or compressive forces, see FIG. 5.

A thread or yarn making up the majority of a fabric used to make the sock, glove or insole may be from one or more non-conductive materials such as nylon, acrylic, wool, cotton, rayon or the like. These threads or yarns typically have round cross-sections with a diameter of about 0.25 mm to 2 mm. These diameters may be quite different than the diameters of leads 31.

Figure 4A:
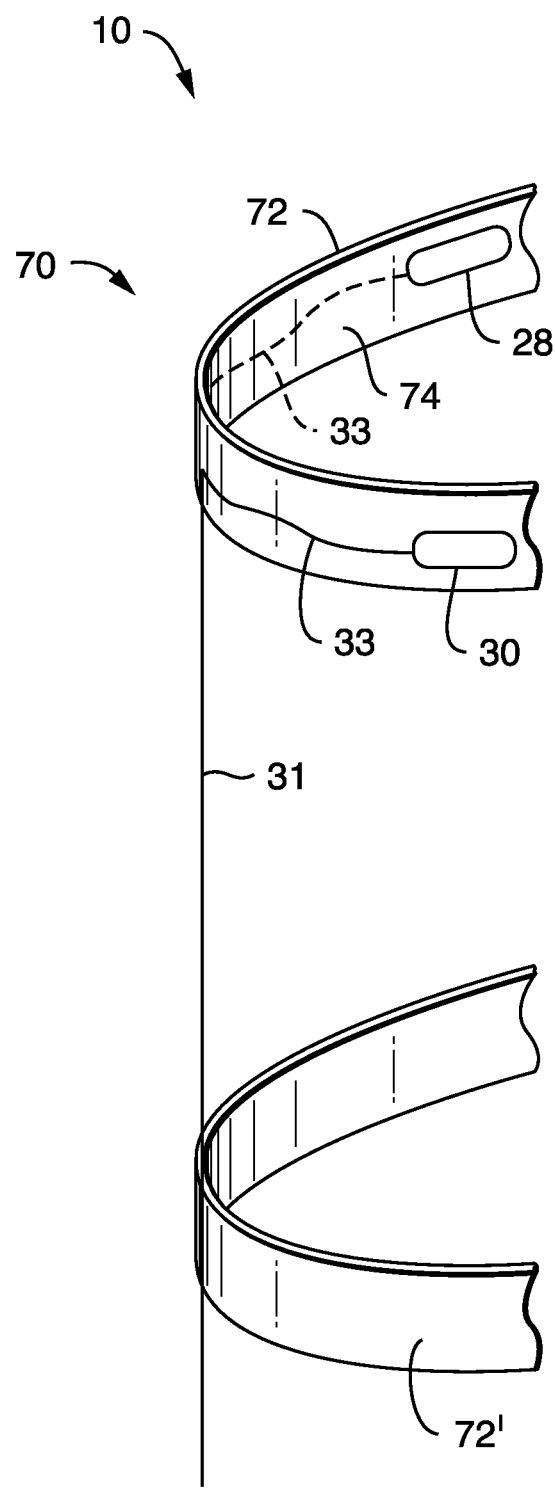
FIG. 4A is a side perspective view of one embodiment of a harness according to the present disclosure.

In another alternative, the support is a simple harness system 70 as shown in FIG. 4A. The harness system 70 has at least one pair of flexible U-shaped collars 72 and 72' connected by a lead 31. The collars 72 have an inner body-facing surface 74, see FIG. 4A. The outer collar 72 has an electrode pair (electrode 28 and 30, in a spaced apart fashion) attached thereto, such as by an adhesive. Leads 33 are attached to the electrodes 28 and 30, and in turn connect to a main lead 31. Referring to FIG. 4C main lead 31 is only mechanically connected to the inner collar 72', and then electrically connected to a as stimulation system 80 that includes a controller and a power supply (not shown). Desirably, the stimulation system 80 may be attached to a band 82 so that it may be placed on the body near the fingers or toes, e.g at the wrist or foot respectively.

Figure 4B:
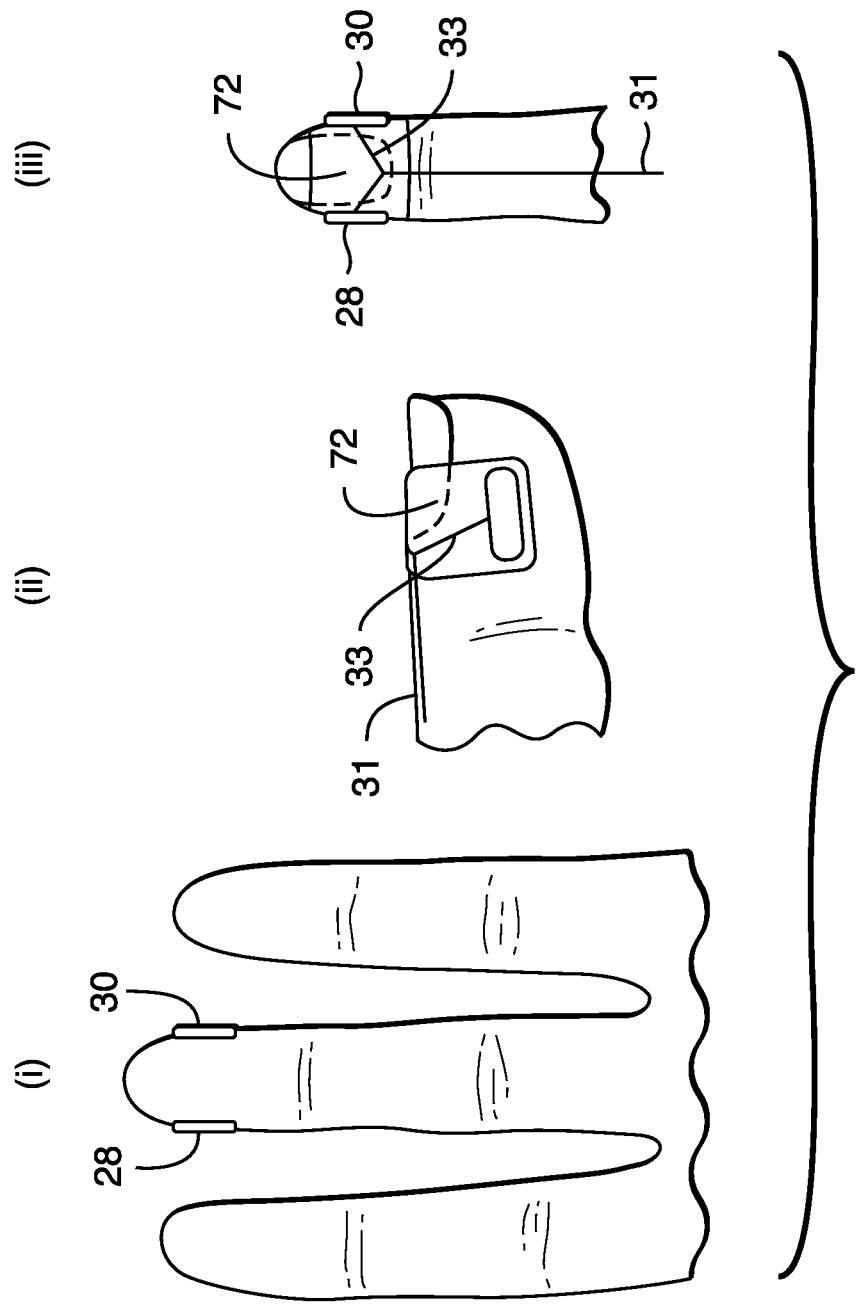
FIG. 4B (i-iii) are bottom, side and top views of the harness as it is attached to a finger.

Each collar engages a finger (or toe) by a compressive force, with a skin-safe adhesive applied to the body-facing surface, or both. Altogether, there may be one to five pairs of collars, one pair for each finger or toe to be stimulated. In one example, as seen in FIG. 4B(i-iii), the outer collar 72 is placed at the distal phalanx of the finger (or toe) so that the electrodes 28 and 30 make contact with the medial and lateral surfaces of the finger (or toe). Therefore, the electrodes 28 and 30 are located on the sock or glove so they make contact with the distal phalanx of the finger/toe at the medial and lateral surfaces of the finger/toe.

Figure 3:
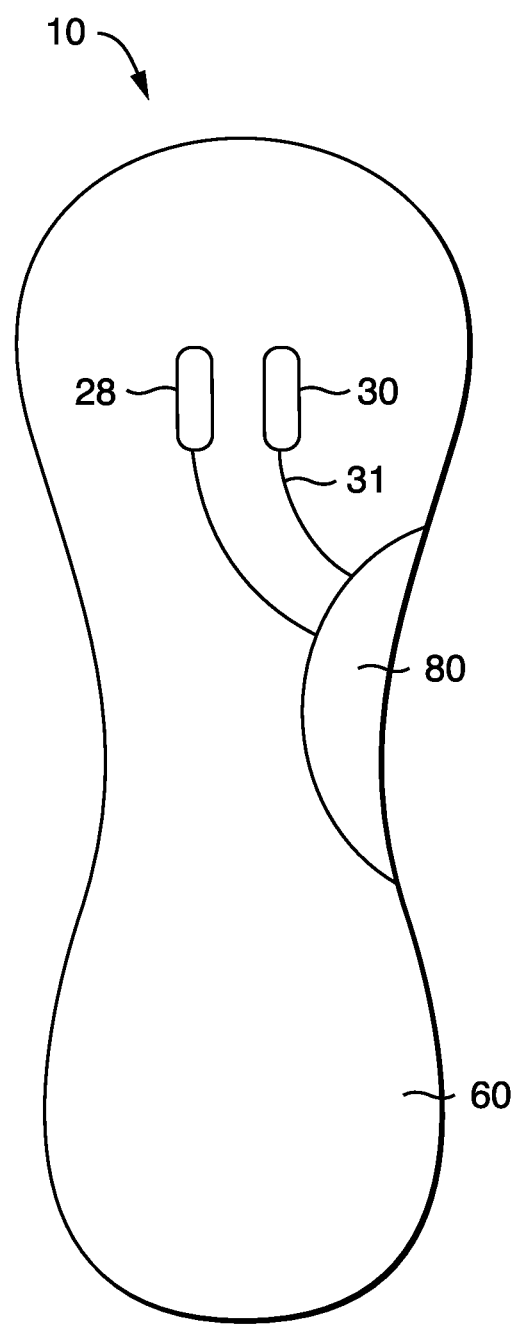
FIG. 3 is a plan view of one embodiment of an insole according to the present disclosure.

Referring to FIG. 3, in the insole embodiment of the present disclosure, at least one pair of electrodes 28 and 30 are located on the insole 60 in a spaced apart manner. Together, the electrodes 28 and 30 to form a pattern will make contact with a sensitive skin area of the foot to enable the user to maintain a balanced state. Desirably, the stimulation system 80 is located at a position that will contact the user's arch when in use.

Power Supply

Figure 9:
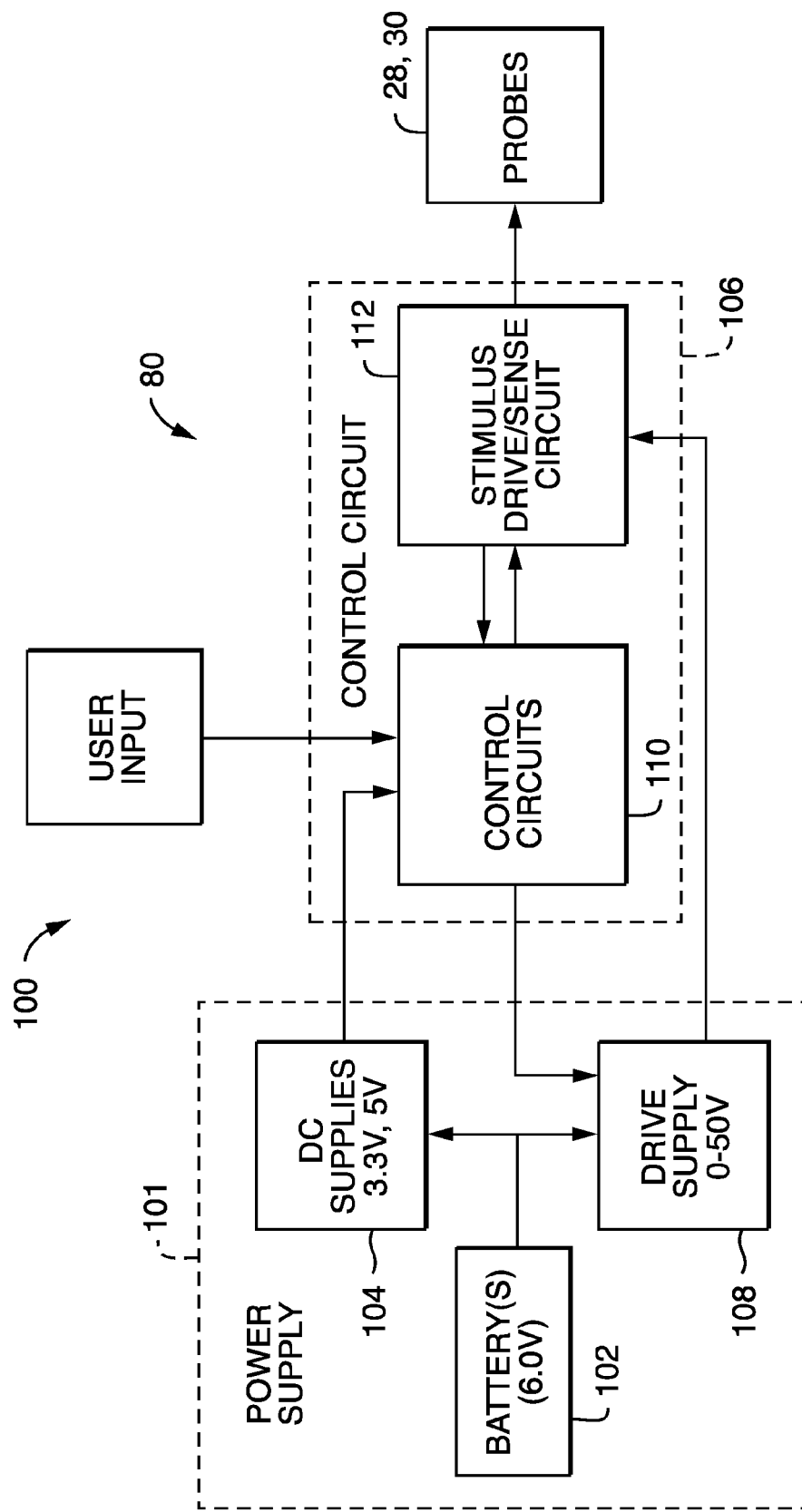
FIG. 9 is a schematic of the power and control system of the present disclosure.

The control and power system 100 of the present disclosure are shown in FIG. 9. A power supply 101 is used to supply voltage to electrode 28. Desirably, the power supply is battery powered by a battery 102, is wearable on the body, light weight, and possibly even waterproof (i.e. to 10 meters) and shock proof (i.e. 10 G). The battery 102 may be powered by primary or secondary cells. One exemplary power supply uses two 3 VDC batteries with 3.3 VDC and 5 VDC regulators 104 to drive control circuitry, shown as controller 106. The batteries 102 may also source a 0-50V drive supply 108.

Desirably, the power supply 101 features include (1) short circuit protection, (2) stable voltage regulation under transient conditions, and (3) current limiting. Other desirable power supply features may include (1) a sleep mode that minimizes power to control circuits and shuts down power to electrode drive circuits, (2) smart indication of low battery, and (3) high efficiency operation for longer battery life.

The exact type of battery cells used herein are not critical. Small camera/watch type batteries that are disposable or rechargeable may be employed. In another aspect, thin printed batteries may be used. Examples of printed batteries are found in the following patents and publications are incorporated herein to the extent they are consistent with the present disclosure: U.S. Pub. No. 2012/0107666 by Bailey et al.; U.S. Pub. No. 2012/0171547 by Pennaz et al.; U.S. Pat. No. 8,268,475 issued to Tucholski et al.; and U.S. Pat. No. 8,119,278 issued to Bailey et al.

Controller

The stimulation system of the present disclosure includes the controller 106 to regulate the electrical power emanating from the power supply 101 described above. The controller 106 delivers electrical stimulation to electrodes 28, 30. Desirably, the controller 106 regulates the voltage across the electrodes 28, 30. In another aspect, controller 106 controls the current so it is constant.

The stimulation waveform can be either biphasic or monophasic square-wave pulses or sinusoidal in shape. Electrical stimulation may be delivered in either a monopolar or bipolar stimulation fashion via the stimulus drive/sense circuit 112. The stimulation parameters include:

Current: 0.1 mA to about 5 mA.
Voltage: about 0.1 V to about 50 V.
Frequency: a single frequency maintained at about 150 Hz to about 350 Hz, but most desirably at 250 Hz.
Pulse duration: 50 μs to about 250 μs.

A desirable controller 106 has one or more of the following characteristics: (1) is multi-channeled so as to allow control of more than one electrode pair at different stimulation paradigms, (2) is current limiting to prevent application of current greater than 5 mA, (3) is able to sense electrode impedance for delivery of constant amplitude, and (4) has a memory of settings from previous stimulation sessions, to enable a short verification protocol versus a longer calibration protocol (described below).

The controller 106 generally includes control circuits 110 and the stimulus drive/sense circuit 112. The stimulation system 80 may contain an embedded microcontroller, an example of which is the MICROCHIP® dsPIC30F6010A available from Microchip Technology Inc., Chandler, Ariz., and signal conditioning circuits such as amplifiers, attenuators, switches, and filters for feedback and control signals. Using custom firmware contained within, the microcontroller is able to generate the necessary waveforms and control signal, process feedback signals, store internally or in external memory operational protocols and session parameters, and process any user input.

The stimulus drive/sense circuit 112 converts the low power control signals to higher power stimulus signals applied to the probes. This circuit 112 may consist of amplifiers, attenuators, isolators, and sensors. Conversely, the circuit 112 may provide feedback signals back to the control circuits 110 to stabilize applied voltage based on electrode impedances.

Method of Use

The article (i.e. sock, glove or insole) is used in a dry state, needing only perspiration or an electrolytic paste/gel to transmit electrical input from the electrodes 28, 30 to the skin. It is undesirable to have a wetted article for reasons of comfort and possibly sanitation.

Calibration of an electrode pair is desired prior to each use. To calibrate an electrode pair, the user activates the controller 106. Electrical pulses are delivered to the electrode 28 with increasing amplitude (stepwise, with each step about 3 seconds). The user adjusts the pulses to an amplitude that is 60% of the sensory threshold. That is, the stimulation amplitude is slowly increased until the subject can feel the stimulation (i.e. method of ascending limits). The lowest amplitude that a subject can detect is considered the sensory threshold. The sensitizing stimulation amplitude is 60% of the recorded sensory threshold.

A verification protocol is desired in order to check the calibration of the electrode pairs. A pulse at the sensory threshold is delivered to a first electrode pair. If the user can sense the pulse within 3 seconds, then a sub-threshold pulse is applied. If after 3 seconds the user did not subsequently sense, verification is complete for that electrode pair. This method is repeated for each of the other electrode pairs. If the stimulus was sensed, then the electrode pair is recalibrated.

After the verification protocol is complete, the actual stimulation protocol can begin. The electrical stimulation is applied in a bipolar fashion. The positive electrode 28 may be located on either side of a finger, toe or foot sole, depending on whether the support is a glove, sock or insole, respectively. The negative electrode 30 is spaced apart therefrom.

EXPERIMENT

Nineteen able-bodied study participants (age 50-70 years; mean 60 years) were used in the experiment.

Each participant was subjected to a procedure to determine the minimal mechanical stimulation intensity needed for sensory perception (the "sensory threshold"). In this procedure, vibratory mechanical stimulation was delivered to each subject with and without the simultaneous delivery of a known sensory sub-threshold electrical stimulation (i.e. 250 Hz solitary frequency, or noise). Stimulating sticky pad surface electrodes (15 mm×20 mm; Rhythmlink; Columbia S.C.) were placed on each subject's third finger at the medial and lateral surfaces of the distal phalanx (FIG. 4B). At times, the investigators cut the electrodes to better fit small fingers. Constant-current electrical stimulation was delivered in a bipolar fashion using a controller (model DS5; available from Digitimer Ltd., UK). Two types of stimulation were delivered to each subject: (1) semi-Gaussian noise with a 1 kHz bandwidth (stochastic resonance); and (2) monophasic square-wave pulses at 250 Hz, and 100 μs pulse duration at 4 ms inter-pulse intervals. All stimuli were delivered at 60% of the electrical sensory threshold.

During the experiment, participants sat in an isolation booth designed to attenuate extraneous vibrations and noises from the greater laboratory environment. The participants also wore headphones to cancel sound generated from within the booth.

Figure 7:
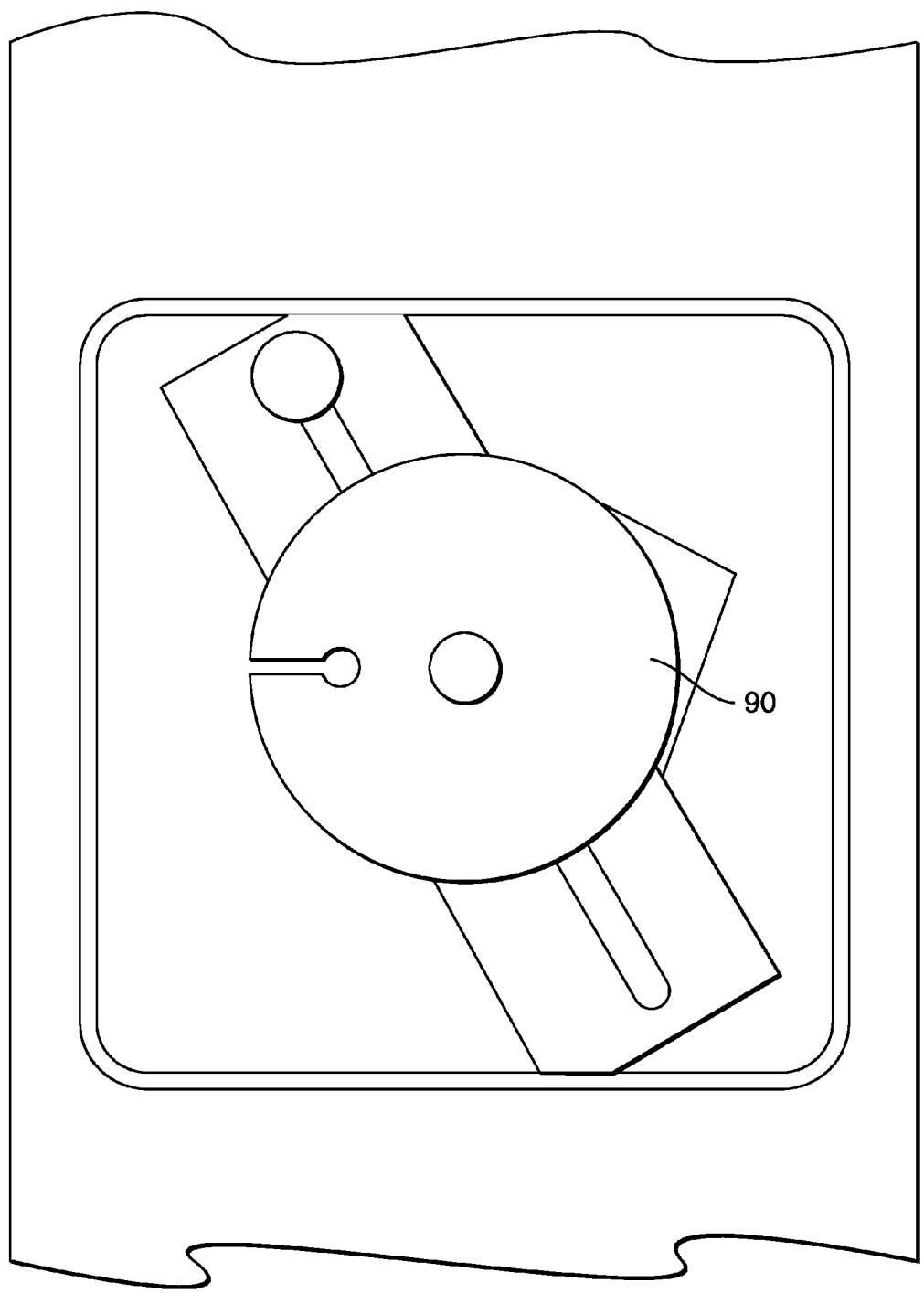
FIG. 7 is a plan view of a contactor used in the experiment described herein.
Figure 8:
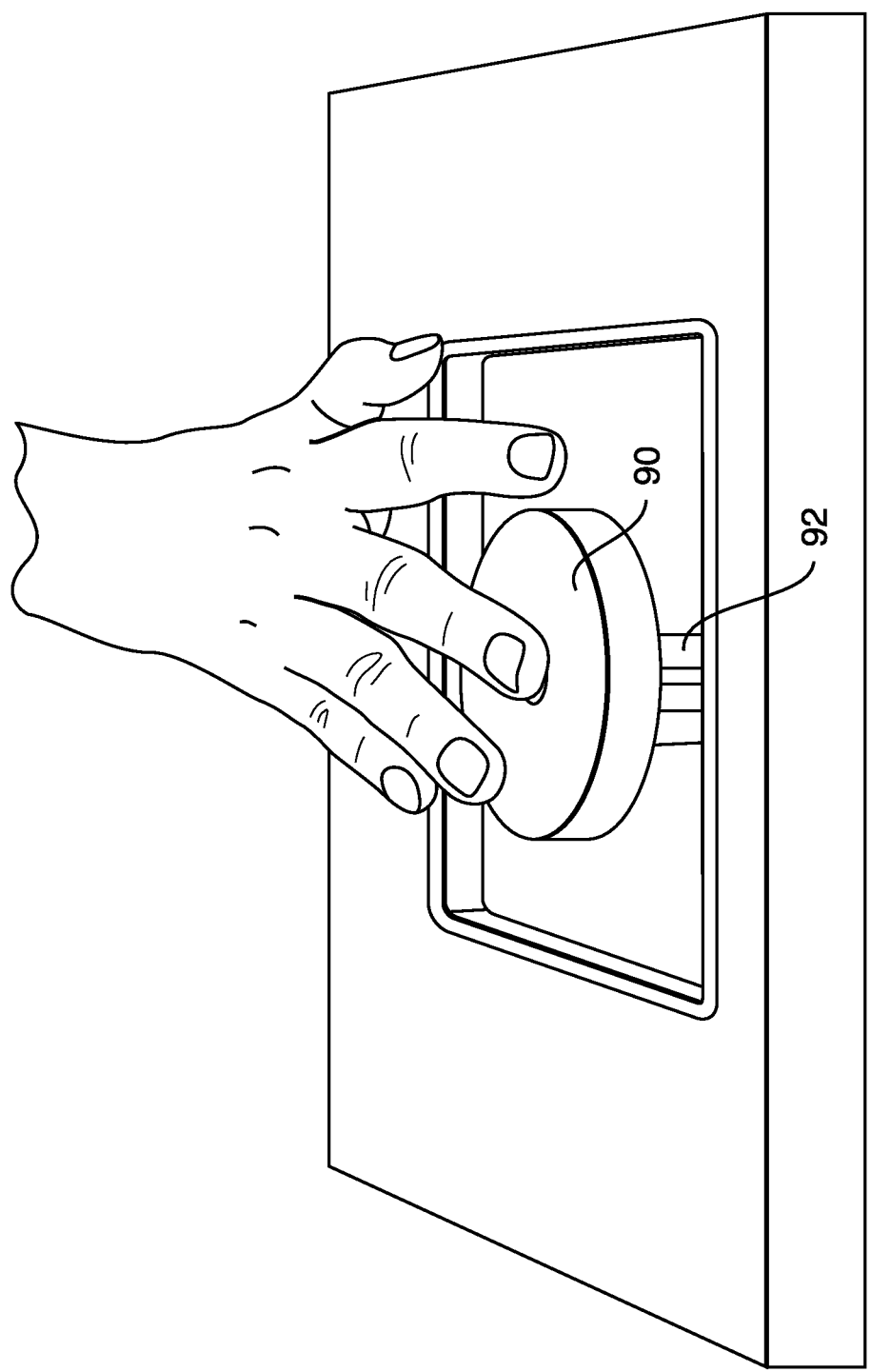
FIG. 8 is a front perspective view of a study participant with a finger contacting the contactor of FIG. 7.

Each participant placed their right arm in a table, pronating their forearm so that their palm faced the floor, see FIG. 8. The participant's fingertip was positioned on a 0.6 cm$^2$ cylindrical contactor 90, see FIG. 7. The contactor 90, heated to body temperature, was mounted on a vibrator (Ling Shaker, Bruel and Kjar VTS, Limited, Naerum, DK) fixed to a rigid support. Mechanical stimulation was applied by a transducer.

A Two-Alternative Forced Choice tracking method was used to determine the minimal mechanical stimulation needed for sensory perception. This method requires participants to choose between two different intervals of stimulation. Presented were two, 1 second stimulation intervals, separated by a non-stimulation period of 1 second. A mechanical signal (250 Hz sinusoidal vibration; 300 ms duration) was applied randomly within one of the two stimulation intervals. The participant indicated which stimulation interval contained the mechanical stimulus. The amplitude of the sinusoidal oscillation was increased by 1 dB (ref. 1 μm) after each incorrect response, and decreased by 1 dB after every third correct response (ignoring incorrect responses). Threshold tracking continued until the range of stimulation intensities repeated itself three times, showing three correct responses followed by an incorrect response. This technique determined the intensity at which the probability of correct responses was 75%. Vibratory mechanical stimulation was delivered to each subject with and without the simultaneous delivery of a sub-threshold electrical stimulation (i.e. 250 Hz monophasic square-wave pulses, or noise).

A mixed-model statistical analysis was used for all comparisons. Results were considered significant at a p<0.05. The results showed that transcutaneous electrical stimulation (250 Hz, monophasic waveform) applied bilaterally to either side of a fingertip can increase tactile sensitivity in the surrounding skin by about 9% (median threshold value: 0.88 μm) as compared to the non-stimulated condition (median threshold value: 0.97 μm). Electrical noise also increased tactile sensitivity (median threshold value: 0.82 μm). However no differences were determined between stimulation types (i.e. 250 Hz vs. Noise). Therefore, one advantage of the present disclosure is that the stimulation can be delivered through a much smaller apparatus.

While the disclosure has been described in detail with respect to the specific embodiments thereof, it will be appreciated that those skilled in the art, upon attaining the understanding of the foregoing, may readily conceive of alterations to, variations of, and equivalents to these embodiments. Accordingly, the scope of the present disclosure should be assessed as that of the appended claims and any equivalents thereto.

The invention claimed is:

1. An article for transcutaneously applying electrical stimulation to sensory receptors comprising:
   a support to which an electrode pair comprising a cathode and an anode;
   single leads attached to each of the positive and negative electrodes, wherein the single leads have insulated coatings; and
   a controller attached to the single leads for delivering monophasic or biphasic electrical stimulation at a single frequency between 150 Hz to 350 Hz, and at a current between 0.1 mA to 5 mA; and
   a power supply connected to the controller.

2. The article of claim 1 wherein the support is a sock, a glove or an insole.

3. The article of claim 2 wherein the sock, the glove or the insole is constructed from a molded material.

4. The article of claim 2 wherein the sock, the glove or the insole is constructed from a nonwoven material.

5. The article of claim 1 wherein the support comprises a harness.

6. The article of claim 1 wherein the power supply is connected to the support.

7. The article of claim 6 wherein the power supply is a flexible battery that can be activated by moisture.

8. The article of claim 1 wherein the electrodes comprise a homogenous layer of a carbon and a polymer blend, the layer having a thickness of less than 100 microns.

9. The article of claim 1 wherein the positive and negative electrodes and each lead comprises a conductive fiber or strip.

10. The article of claim 1 wherein materials from which the positive and negative electrodes are constructed have a different composition than materials from which the single leads are constructed.

11. The article of claim 1 further comprising an electrolytic adhesive located on a body-facing surface of each of the positive and negative electrodes.

12. The article of claim 11 further comprising a dome member having a concave surface to which the positive electrode or the negative electrode is attached, wherein the electrolytic adhesive is applied to the concave portion so that it covers a bodyfacing surface of the corresponding positive or negative electrode.

13. The article of claim 1 further comprising a second electrode pair electrically connected to the controller.

14. The article of claim 13 wherein the controller is multichanneled so that the electrode pairs can be independently controlled.

15. A method of transcutaneously stimulating sensory receptors of the human body comprising the steps of:
   contacting the intact skin of a human with an electrode pair comprising a positive electrode spaced apart from a negative electrode; and
   delivering monophasic or biphasic electrical current to the positive electrode at a single frequency of between 150 Hz to 350 Hz.

16. The method of claim 15 wherein the electrical current is less than 5 mA.

17. The method of claim 15 wherein an electrolytic gel or paste is disposed between the skin and the positive electrode, and the skin and the negative electrode.

18. The method of claim 15 wherein the electrical current is delivered in square pulses having a duration of about 100 s.

19. The method of claim 15 wherein the positive electrode is disposed on the concave surface of a collapsible dome, and the dome is collapsed causing the positive electrode to contact the intact skin.

20. The method of claim 15 wherein there is a constant voltage across the electrode pair.

* * * * *